United States Patent
Thames et al.

(10) Patent No.: US 6,897,257 B2
(45) Date of Patent: May 24, 2005

(54) PROCESS FOR FORMING LATEX POLYMERS

(75) Inventors: Shelby F. Thames, Hattiesburg, MS (US); Oliver W. Smith, Petal, MS (US); Sheng Chen, Shanghai (CN); Catherine C. Blackwell, Hattiesburg, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 173 days.

(21) Appl. No.: 10/118,586

(22) Filed: Apr. 8, 2002

(65) Prior Publication Data

US 2003/0045609 A1 Mar. 6, 2003

Related U.S. Application Data

(63) Continuation-in-part of application No. 09/460,946, filed on Dec. 14, 1999, now Pat. No. 6,624,223, which is a continuation-in-part of application No. 08/773,741, filed on Dec. 24, 1996, now Pat. No. 6,203,720.

(51) Int. Cl.$^7$ .................. C08L 33/04; C08L 33/14; C08L 31/04; C08F 2/22; C07C 59/40
(52) U.S. Cl. .................. 524/556; 524/563; 524/801; 554/219
(58) Field of Search .................. 524/556, 560, 524/563, 505, 801; 554/219, 227

(56) References Cited

U.S. PATENT DOCUMENTS

| | | | |
|---|---|---|---|
| 2,593,444 A | * 4/1952 | Harrison | 526/329.1 |
| 3,010,925 A | * 11/1961 | Lynn | 524/313 |
| 3,714,100 A | 1/1973 | Biale et al. | 260/29.6 |
| 3,952,032 A | 4/1976 | Vrancken et al. | 260/404.8 |
| 3,993,612 A | * 11/1976 | Aihara et al. | 524/559 |
| 4,048,136 A | 9/1977 | Kobayashi et al. | 260/42.14 |
| 4,131,580 A | 12/1978 | Emmons et al. | 260/29.6 |
| 4,141,868 A | 2/1979 | Emmons et al. | 260/23 |
| 4,144,212 A | 3/1979 | Linder et al. | 260/29.7 |
| 4,226,754 A | 10/1980 | Yun et al. | 260/29.6 |
| 4,261,872 A | 4/1981 | Emmons et al. | 260/22 |
| 4,289,675 A | 9/1981 | Krajewski | 260/29.6 |
| 4,356,128 A | 10/1982 | Rogier | 260/465.6 |
| 4,540,739 A | 9/1985 | Midgley | 524/764 |
| 4,626,582 A | 12/1986 | Virnig et al. | 526/298 |
| 4,745,213 A | 5/1988 | Schlosser et al. | 560/217 |
| 4,791,167 A | 12/1988 | Saukaitis | 524/544 |
| 4,803,252 A | 2/1989 | Kida et al. | 526/297 |
| 4,826,907 A | 5/1989 | Murao et al. | 524/394 |
| 4,906,684 A | 3/1990 | Say | 524/548 |
| 5,122,567 A | 6/1992 | Spada et al. | 524/818 |
| 5,243,069 A | 9/1993 | Emmons | 560/224 |
| 5,288,807 A | 2/1994 | Hinz | 525/279 |
| 5,312,889 A | 5/1994 | Frische et al. | 528/74.5 |
| 5,362,816 A | 11/1994 | Snyder et al. | 525/329.9 |
| 5,435,879 A | 7/1995 | Knutson et al. | 156/327 |
| 5,733,970 A | * 3/1998 | Craun | 524/811 |
| 5,750,751 A | * 5/1998 | Saam | 554/165 |
| 6,001,913 A | 12/1999 | Thames et al. | 524/398 |
| 6,140,435 A | * 10/2000 | Zanotti-Russo | 526/238.2 |
| 6,174,948 B1 | 1/2001 | Thames et al. | 524/398 |
| 6,203,720 B1 | 3/2001 | Thames et al. | 252/182.12 |

FOREIGN PATENT DOCUMENTS

| | | |
|---|---|---|
| EP | 319608 A1 * | 6/1989 |
| EP | 0 466 409 A1 | 1/1992 |
| IN | 154467 | 7/1980 |
| IN | 153599 | 6/1981 |
| IN | 154647 | 8/1981 |

OTHER PUBLICATIONS

"Castor–Based Derivatives: Synthesis of Some Acrylate Esters" by Jane S. Nelson and Thomas H. Applewhite, *Journal of the American Oil Chemists' Society*, Sep., 1966, pp. 542–545.

* cited by examiner

*Primary Examiner*—Callie Shosho
(74) *Attorney, Agent, or Firm*—Howrey, Simon, Arnold & White, LLP

(57) ABSTRACT

A process for synthesizing copolymers of ethylenically unsaturated monomers with ethylenically unsaturated derivatives of fatty acids and/or oils via emulsion polymerization techniques is performed in two stages. One or more suitable ethylenically unsaturated monomers are polymerized in the first stage of an emulsion polymerization. The ethylenically unsaturated derivatives of fatty acids and/or oils are blended with other monomers and polymerized in a second stage of the polymerization reaction. A suitable surfactant is added to the polymerization mixture to facilitate formation of the emulsion. In a preferred embodiment, the surfactant is a hybrid surfactant, i.e., one having both anionic and non-ionic characteristics.

7 Claims, No Drawings

PROCESS FOR FORMING LATEX POLYMERS

This application is a continuation-in-part of application Ser. No. 09/460,946filed Dec. 14, 1999, now U.S. Pat. No. 6,624,223 which is a continuation-in-part of application Ser. No. 08/773,741, filed Dec. 24, 1996 now U.S. Pat. No. 6,203,720.

BACKGROUND OF THE INVENTION

The present invention is directed to a process for forming a latex polymer containing an ethylenically unsaturated derivatives of fatty acids and/or oils. More particularly, the present invention is directed to a process for forming a latex polymer which is produced by a staged polymerization process.

One problem encountered by coatings manufacturers is the development of formulations containing low VOC-coalescing aids or plasticizers. For instance, emulsion polymers are currently formulated with coalescing aids or plasticizers in order to form films at and below ambient conditions yet dry to films of sufficient glass transition temperature ($T_g$) to perform adequately at and above room temperature. In general, the ability of emulsion polymers to form or coalesce into film is governed by the minimum film forming temperature (MFT) of the polymer in question. Low MFT polymers are required in order to exhibit coalescence, flow, and surface wetting properties. However, if the polymer remains soft and tacky, the coatings are not usable. Therefore, it is necessary to develop a technology in which coating formulations contain suitable ingredients to provide an initial low MFT, which, upon application, form nontacky, durable, hard, and water resistant surfaces having a $T_g$ significantly above their MFT.

Various other coating compositions which cure under ambient conditions are known in the prior art. A few such examples involve curing by a chemical reaction such as epoxide-carboxylic acid reaction, isocyanate-moisture reaction, polyaziridine-carboxylic acid reaction, and activated methylene-unsaturated acrylic reaction.

Recently, a number of new latex or emulsion compositions derived from semi-drying and/or non-drying oils have been developed for use in coatings, adhesives and inks. Such compositions are disclosed in U.S. Pat. Nos. 6,001,913; 6,174,948; and 6,203,720 each of which is incorporated herein by reference in its entirety.

The copolymerization of vinyl acetate with ethylenically unsaturated derivatives of fatty acids and/or oils via conventional emulsion polymerization techniques led to surprisingly low molecular weight polymers with poor film properties. Moreover, the uniquely large structure and high molecular weight of the ethylenically unsaturated derivatives of fatty acids and/or oils placed special demands on the surfactant choice.

Accordingly, it would be an advancement in the art to provide an economical process for co-polymerizing an ethylenically unsaturated monomer suitable for forming a latex polymer with ethylenically unsaturated derivatives of fatty acids and/or oils to form polymers that can be used in low VOC latex or emulsion compositions.

SUMMARY OF THE INVENTION

The present invention provides a process for synthesizing copolymers of ethylenically unsaturated monomers with ethylenically unsaturated derivatives of fatty acids and/or oils via emulsion polymerization techniques.

In a preferred embodiment, the present invention comprises a staged polymerization reaction in which one or more suitable ethylenically unsaturated monomers are polymerized in the first stage of an emulsion polymerization. Suitable monomers include, but are not limited to, at least one copolymerizable monomer selected from the group consisting of vinyl acetate, vinyl chloride, vinyl ester of a saturated tertiary branched carboxylic acid, acrylonitrile, acrylamide, 2-ethylhexyl acrylate, 2-ethylhexyl methacrylate, 2-hydroxyethyl acrylate, 2-hydroxyethyl methacrylate, glycidyl acrylate, glycidyl methacrylate, acrylic acid, methacrylic acid, butyl acrylate, butyl methacrylate, methyl methacrylate, methyl acrylate, para-acetoxystyrene, and styrene.

The ethylenically unsaturated derivatives of fatty acids and/or oils are blended with other monomers and polymerized in a second stage of the polymerization reaction.

A suitable surfactant is added to the polymerization mixture to facilitate formation of the emulsion. In a preferred embodiment, the surfactant comprises a hybrid surfactant, i.e., one having both anionic and non-ionic characteristics.

DETAILED DESCRIPTION

The present invention provides a process that can be used to form latex and emulsion polymers useful in coatings, adhesives and inks having essentially no VOCs. In the preferred embodiment, the process involves the staged polymerization of suitable ethylenically unsaturated monomer(s) and ethylenically unsaturated derivatives of fatty acids and/ or oils. The latter can function as an internally plasticizing compound.

The monomers useful in this invention include polymerizable acid monomers, and various other ethylenically unsaturated monomers well known in the art.

Polymerizable acid monomers that can be used in this invention are the well known mono- or polycarboxylic acids which contain at least one polymerizable bond per molecule. Examples of such acids are acrylic acid, methacrylic acid, maleic acid, fumaric acid, itaconic acid, ethacrylic acid, crotonic acid, citraconic acid, and half esters of the dicarboxylic acids wherein the esterified alcohol group contains from 1 to about 20 carbon atoms. Examples of suitable half esters are methyl hydrogen maleate, methyl hydrogen fumarate, benzyl hydrogen maleate, butyl hydrogen maleate, octyl hydrogen itaconate, dodecyl hydrogen citraconate, and the like. Carboxylic acid anhydrides such as maleic anhydride can also be used. The preferred acids for use in this invention are acrylic and methacrylic acids.

Additional monomers that contain at least one ethylenically unsaturated polymerizable group that can be used in the present invention include acrylic and methacrylic esters wherein the ester group contains 1 to about 20 carbon atoms, e.g., methyl acrylate, methyl methacrylate, ethyl acrylate, ethyl methacrylate, isopropyl acrylate, isopropyl methacrylate, butyl acrylate, butyl methacrylate, 2-ethylhexyl methacrylate, decyl acrylate, lauryl methacrylate, benzyl acrylate, and the like. Esters of various other unsaturated acids include butyl fumarate, octyl fumarate, butyl maleate, and octyl maleate.

Other acrylic or methacrylic esters which can be used in this invention are multifunctional acrylates or methacrylates, and include, for example, propylene glycol monoester of acrylic acid, propylene glycol monoester of methacrylic acid, ethylene glycol monoester of acrylic acid, ethylene glycol monoester of methacrylic acid, glycidyl acrylate, glycidyl methacrylate, hydroxyethyl acrylate, hydroxyethyl methacrylate, and hexanediol diacrylate.

Other suitable monomers are vinyl aromatic monomers, such as styrene, para-acetoxystyrene, vinyl toluene, alpha methyl styrene, vinyl pyridine and the like as well as nitriles and amides, e.g., acrylonitrile and acrylamide. Other olefinic monomers such as ethylene, propylene, and butadiene are also suitable comonomers for this invention.

Additional monomers that can be used in this invention are the derivatives of the hypothetical vinyl alcohol, i.e., aliphatic vinyl esters such as vinyl formate, vinyl acetate, vinyl propionate, vinyl butyrate, vinyl heptanoate, vinyl pelargonate, vinyl 3,6-dioxaheptanoate, vinyl 3,6,9-trioxaundecanoate, the vinyl ester of versatic acid (sold under the tradenames Veova 10™, EXXAR 10 and EXXAR 12), $C_5$–$C_{12}$ saturated tertiary branched carboxylic acids, vinyl esters of neo acids and the like. Other vinyl monomers such as vinyl chloride, vinyl sulfonate, and vinylidene chloride are also suitable comonomers.

Various other copolymerizable monomers that impart enhanced properties to the resulting compositions of the present invention may also be used. One such example is a wet adhesion promoter which improves adhesion of the compositions to a wide variety of substances including wood, plastic, and metal surfaces. Illustrative examples of such wet adhesion promoting monomers include dimethylaminoethyl methacrylate, methacrylamidoethylethyleneurea (sold under the tradename Sipomer® WAM II by Rhone-Poulenc), acrylamidoethylethyleneurea, 3-isopropenyl-α,α-dimethylbenzyl isocyanate, and styrene sulfonate.

Further monomers include silanes such as vinyltriisopropoxysilane, gamma-methacryloxypropyltriisopropoxysilane, vinyltrimethoxysilane, gamma-methacryloxypropyltrimethoxysilane and vinyltrimethoxysilane.

The types and amounts of monomers used in this invention will vary depending on the particular end use for which the product of this invention is intended. Such variations are well known and can be readily determined by those skilled in the art. In general, the weight percents of the internally plasticizing compound, i.e., the ethylenically unsaturated derivatives of fatty acids and/or oils and the ethylenically unsaturated monomer in the resulting composition range from about 5 and not more than about 80 weight percent based upon the total weight of the composition. Preferably, the total weight percents range from about 30 to about 70 weight percent based on the total weight of the composition. The weight ratio of the ethylenically unsaturated fatty acid derivative to the ethylenically unsaturated monomer(s) generally ranges from about 1:2 to about 1:99, preferably the weight ratio ranges from about 1:7 to about 1:20.

Ethylenically unsaturated monomers are polymerized in the first stage of an emulsion polymerization. As described hereinbelow, the compositions of this invention are prepared by polymerization of monomers emulsified in water using conventional emulsion polymerization procedures. Suitable surface-active agents generally known as surfactants are used for emulsification of the monomers. Suitable surfactants include cationic, anionic, amphoteric, or nonionic surfactants and hybrids or mixtures thereof.

Examples of useful cationic surfactants include alkylamine salts such as laurylamine acetate, quaternary ammonium salts such as lauryl trimethyl ammonium chloride and alkyl benzyl dimethylammonium chlorides, and polyoxyethylenealkylamines.

Examples of useful anionic surfactants are organosulfates and sulfonates, e.g., sodium and potassium alkyl, aryl, and aralkyl sulfates and sulfonates, such as sodium 2-ethylhexyl sulfate, potassium 2-ethylhexyl sulfate, sodium nonyl sulfate, sodium lauryl sulfate, potassium methylbenzene sulfonate, sodium dodecylbenzene sulfonate, potassium toluene sulfonate, ammonium salts of nonylphenolethoxyl sulfonates and sodium xylene sulfonate; higher fatty alcohols, e.g., stearyl, lauryl, etc., which have been ethoxylated and sulfonated; dialkyl esters of alkali metal sulfosuccinic acid salts, such as sodium diamyl sulfosuccinate, sodium dioxtyl sulfosuccinate, and sodium dioctyl sulfosuccinate, formaldehyde-naphthalene sulfonic acid condensation products; and alkali metal salts, partial alkali metal salts and free acids of complex organic phosphate esters.

Examples of the amphoteric surfactants are alkylbetaines such as lauryl-betaine.

Examples of nonionic surfactants which can be used in this invention are polyethers, e.g., ethylene oxide and propylene oxide condensates which include straight and branched chain alkyl and alkaryl polyethylene glycol and polypropylene glycol ethers and thioethers; alkylphenoxypoly(ethyleneoxy) ethanols having alkyl groups containing from about 7 to about 18 carbon atoms and having from about 4 to about 240 ethyleneoxy units, such as heptylphenoxypoly(ethyleneoxy) ethanols, nonylphenoxypoly(ethyleneoxy) ethanols; the polyoxyalkylene derivatives of hexitol including sorbitans, sorbides, mannitans and mannides; partial long-chain fatty acids esters, such as the polyoxyalkylene derivatives of sorbitan monolaurate, sorbitan monopalmitate, sorbitan monostearate, sorbitan tristearate, sorbitan monooleate and sorbitan trioleate; the condensates of ethylene oxide with a hydrophobic base, said base being formed by condensing propylene oxide with propylene glycol; sulfur containing condensates, e.g., those prepared by condensing ethylene oxide with higher alkyl mercaptans, such as nonyl, dodecyl, or tetradecyl mercaptan, or with alkylthiophenols wherein the alkyl group contains from about 6 to about 15 carbon atoms; ethylene oxide derivatives of long-chain carboxylic acids, such as lauric, myristic, palmitic, or oleic acids or mixtures of acids, such as tall oil fatty acids; ethylene oxide derivatives of long-chain alcohols such as octyl, decyl, lauryl, or cetyl alcohols; and ethylene oxide/propylene oxide copolymers sold under the tradename Pluoronics™.

A particularly preferred surfactant for use in this invention is a hybrid surfactant, i.e., a surfactant having both anionic and non-ionic characteristics. Examples of suitable surfactants include Rhodapex CO 436™, and Abex® EP-100 manufactured by Rhodia.

The amounts of surfactants employed in the emulsion polymerization process will range from about 0.01 to about 10 weight percent, preferably about 0.2 to about 5 weight percent based on the total weight of monomers.

After polymerization of the monomers is complete or essentially complete, the ethylenically unsaturated carboxylic acid or acid ester derived from the semi-drying or non-drying oil is added to the emulsion and polymerized in a second stage, optionally with other monomers.

The preferred monomers suitable for forming the latex or emulsion compositions of this invention are derivatives of semi- or non-drying oils having an ethylenically unsaturated ester of a long-chain olefinic compound. Preferred monomers of this invention are acrylate or methacrylate esters of long-chain olefinic monomers derived (or obtained) from either castor oil, soybean, dehydrated castor or lesquerella oils. The latices formed by this invention have utility in numerous applications such as in coatings, adhesives, and inks formulations.

The term "derived" used herein is intended to mean that the monomers of the present invention are obtained or formed from a wide variety of semi- or non-drying oils. Various chemical and physical modifications of these semi- or non-drying oils may be made to obtain the desirable monomers, dimers, trimers and other oligomers of the present invention using methods well known in the art.

Various semi- and non-drying oils may be employed for the formation of the monomers of the present invention. Generally, oils are classified as drying, semi-drying, or non-drying based on their "iodine value," that is, the number of grams of iodine required to saturate the double bonds of 100 grams of an oil. In accordance with this definition, oils having an iodine value of about 120 to 150 are generally considered to be semi-drying oils, and oils having less than 120 are generally considered to be non-drying oils. Illustrative examples of such semi-drying oils include safflower oil, sunflower oil, soybean oil, and tobacco seed oil. Illustrative examples of such non-drying oils include cottonseed oil, coconut oil, rapeseed oil, castor oil, and lesquerella oil. A detailed description of the classification of various oils may be found in "*Surface Coatings—Raw Materials and Their Usage,*" Vol. I, Chapman and Hall, Chapter 4, p-45, (1993), incorporated herein by reference in its entirety.

Saturated or unsaturated fatty acid chain means any of the variety of long-chain fatty acids present in the oils as one of the triglycerides. These fatty acids may further be substituted by one or more substituents selected from the group consisting of alkyl, alkoxy, alkoxyalkyl, hydroxy, hydroxyalkyl, acyloxyalkyl, and halogens. Illustrative examples of a few of these fatty acids include oleic acid, elaidic acid, linoleic acid, linolenic acid, erucic acid, brassidic acid, nervonic acid, lauric acid, myristic acid, palmitic acid, margaric acid, stearic acid, arachidic acid, behenic acid, lignoceric acid, cerotic acid, melissic acid and undecylenic acid.

The invention can be further understood by reference to the following illustrative examples.

EXAMPLE 1

Staged emulsion polymerization was performed in a one-liter cylindrical reactor equipped with a nitrogen purge system, condenser, metallic stirrer, initiator feed, and pre-emulsion feed. The reactor was maintained at a constant temperature by utilizing a water bath. The reactor was charged with 90.00 grams of deionized (DI) water, 0.30 grams of QP-300, 0.78 grams of Rhodapex CO-436™ and 1.93 grams of Igepal CO-887™ and stirred until homogeneous. The reactor was immersed in the water bath at 60° C., purged with nitrogen for 20 minutes while stirring to produce a vortex. After purging, the nitrogen inlet valve was turned off so that a nitrogen head was maintained over the reaction. Stage I pre-emulsion was prepared by adding 130.00 grams of DI water, 0.65 grams of ammonium bicarbonate, 1.93 grams of Rhodapex CO-436™ and 4.80 grams of Igepal CO-887™ to a 1000 mL glass bottle and magnetically stirring it till it became homogeneous. While stirring, 182.28 grams of vinyl acetate and 111.72 grams of butyl acrylate were added to the mixture. After magnetically stirring for 5 minutes, the mixture was agitated at 1600 rpm for another 20 minutes by using a high-speed industrial mixer. Stage II pre-emulsion was prepared by adding 30.00 grams of DI water, 0.35 grams of ammonium bicarbonate, 0.52 grams of Rhodapex CO-436™ and 1.29 grams of Igepal CO-887™ to a 200 mL glass bottle and stirring magnetically until the mixture became homogeneous. The mixture was then stirred at 1200 rpm with a high-speed industrial mixer. While stirring, 6.00 grams of acrylated castor oil methyl esters ("CAM") were added and the mixture was stirred at 1800 rpm for another 20 minutes. The dispersibility of the Stage II pre-emulsion is critical for the incorporation of CAM into the latex and was checked by adding a drop of the pre-emulsion to water in a small vial. When adequately dispersed, the pre-emulsion disperses in water without forming visible droplets of oil.

Initiator solutions consist of two components, oxidizer and reducer. In a 200 mL glass bottle, 0.574 grams of ammonium persulfate and 1.022 grams of t-butyl hydroperoxide were mixed with 30.0 grams of DI water to prepare the oxidizing agent. The reducing agent was prepared by mixing 1.123 grams of Bruggollite FF 6™ and 30.0 grams of DI water in another 200 mL glass bottle. The initiator solutions were agitated until the solid components dissolved completely. The initiator solutions were then transferred to syringes and introduced separately via a syringe pump to the reaction.

The reactor stirrer was set to 250 rpm and the pre-seeding reaction was conducted by adding 6% by weight (26.36 grams) of the pre-emulsion solution from the Stage I pre-emulsion and 20% by weight of the initiator solutions (6.0 mL of oxidizer and reducer each). After pre-seeding for 20 minutes and observation of an exotherm, the remaining Stage I pre-emulsion and initiator solutions were fed into the kettle at constant rates over 3.0 hours and 4.0 hours, respectively. After the initiator solution for Stage I has been added, the residual vinyl acetate monomer should be less than 3000 ppm, preferably less than 1000 ppm.

Stage II pre-emulsion and initiator solutions (8.0 mL) were then fed into the kettle at constant rates over 0.50 hours and 1.75 hours, respectively. After initiator addition was completed, the reaction was heated for an additional 30 minutes to complete the polymerization. The latex was removed from the water bath, cooled to room temperature and filtered through a Gardco® fine filter (60×48) and stored for subsequent use.

EXAMPLE 2

When the above procedure was repeated without adequately dispersing the Stage II pre-emulsion, the latexes that were produced exhibited a yellow layer on the surface that was identified as CAM.

EXAMPLE 3

Staged emulsion polymerization was performed in a 75 gallon cylindrical reactor equipped with a nitrogen purge system, condenser, metallic stirrer, initiator feed, and pre-emulsion feed and maintained at a constant temperature of 60° C. The reactor was charged with 69.0 pounds of DI water, 0.230 pounds of QP-300™, 0.60 pounds of Rhodapex CO-436™ and 1.48 pounds of Igpal CO-887™ and stirred until homogeneous. The agitation was set for 100 rpm and the nitrogen flow rate was maintained for 1 CFH during the whole reaction. Stage I pre-emulsion was prepared by mixing 100.00 pounds of DI water, 0.50 pounds of ammonium bicarbonate, 1.48 pounds of Rhodapex CO-$_{436}$™ and 3.68 pounds of Igepal CO-887™ in an appropriate container and stirring it till the mixture became homogeneous. While stirring, 139.77 pounds of vinyl acetate and 85.66 pounds of butyl acrylate were added to the mixture and stirred for another 20 minutes. Stage II pre-emulsion was prepared by mixing 23.0 pounds of DI water, 0.27 pounds of ammonium bicarbonate, 0.40 pounds of Rhodapex CO-436™ and 0.99 pounds of Igepal CO-887™ in an appropriate container and stirring the mixture till it became homogeneous. While stirring vigorously, 4.60 pounds of CAM was added to the mixture and then the mixture was stirred for another 15 minutes. The dispersibility of the Stage II pre-emulsion is critical for the incorporation of CAM into the latex and was checked by adding a drop of the pre-emulsion to water in a small vial. When adequately dispersed, the pre-emulsion disperses in water without forming visible droplets of oil.

Initiator solutions consist of two components, oxidizer and reducer. The oxidizer solution was prepared by mixing 0.45 pounds of ammonium persulfate and 0.80 pounds of t-butyl hydroperoxide with 23.8 pounds of DI water in a 5-gallon container. The reducer was prepared by mixing 0.89 pounds of Bruggollite FF 6™ with 23.8 pounds of DI water in another 5-gallon container. The initiator solutions were agitated till the solid components dissolved and then introduced by syringe pump to the reaction separately. When the reactor temperature reached 55° C., the pre-seeding reaction was initiated by adding 6% by weight (19.86 pounds) of the pre-emulsion solution from the Stage I pre-emulsion and 20% by weight (4.8 pounds each of oxidizer and reducer) of the initiator solutions for 20 minutes at 100 rpm agitation. After pre-seeding and observation of an exotherm, the remaining Stage I pre-emulsion and initiator solutions were fed into the reactor at constant rates at 60° C. over 3.0 hours and 4.5 hours, respectively. After 2.5 hours of monomer addition, the residual vinyl acetate monomer was reduced to 64,000 ppm. The residual vinyl acetate monomer reduced to 2025 ppm when the initiator addition was completed.

Stage II pre-emulsion and initiator solutions (6.35 pounds of oxidizer and 6.19 pounds of reducer) were then fed into the kettle at constant rates over 0.5 hour and 1.0 hour, respectively. The latex was cooled to 40° C. within 30 minutes. Then 0.24 pounds of defoamer Colloid 581B™ and 0.34 pounds of biocide 1.5% Kathon-LX 150™ (Rohm & Haas Company) were added to the mixture while stirring. The emulsion was filtered through a 200 mesh screen filter and stored for subsequent use. The amount of residual vinyl acetate in the final product was 1574 ppm.

EXAMPLE 4

A staged vinyl-acrylic latex was formulated in which vinyl acetate, butyl acrylate and acrylic acid are polymerized in the first stage and butyl acrylate and CAM are introduced in stage II. The weight ratio of stage I to stage II was 70/30. The emulsion polymerization was conducted in a one-liter latex reactor system equipped with a nitrogen purge, condenser, and mechanical stirrer. The reactor was charged with 104.0 grams of deionized (DI) water and 2.0 grams of Rhodapex CO-436™ (ammonium salt of sulfated polyethoxynonylphenol with 4 moles of ethylene oxide units; obtained from Rhodia), placed in a water bath at 80° C. and purged with nitrogen for 30 minutes. An initiator solution consisting of 40.0 grams of water and 1.6 grams of ammonium persulfate was prepared. Pre-seeding was achieved by the addition of 21.0 grams of vinyl acetate, 9.0 grams of butyl acrylate and 10.0 mL of the initiator solution. The pre-seeding mixture was allowed to react for 20 minutes.

The monomers for stage I were pre-emulsified by first dissolving 5.0 grams of Rhodapex CO-436™ and 0.4 grams of sodium carbonate in 104.0 grams of DI water. Next, 147.0 grams of vinyl acetate, 63.0 grams of butyl acrylate, and 1.5 grams of acrylic acid were added while stirring. The mixture was then stirred at 1500 rpm for 15 minutes. The stage I pre-emulsion was added over a period of 2.1 hours and 20.5 mL of the initiator solution was added over a period of 2.3 hours. The initiator addition was completed prior to beginning stage II.

Monomers for stage II were pre-emulsified by first dissolving 10.0 grams of Rhodapex CO-436™ and 0.6 grams of sodium carbonate in 60 grams of DI water. Next, 75.0 grams of butyl acrylate, 15.0 grams of CAM were added and the mixture was stirred at 1500 rpm for 15 minutes. The stage II pre-emulsion was added to the reaction kettle over a period of 0.95 hours. The remaining 9.5 mL of the initiator solution was added over a period of 1.05 hours.

Redox chaser solutions [prepared from 5.0 grams of DI water and 0.3 grams of sodium formaldehyde sulfoxylate (SFS) as the reducer and 5 grams of DI water and 0.45 grams of tert-butyl hydroperoxide (70% in water) as the oxidizer] were added to reduce residual monomer. Half the chaser solution was added at the end of stage I and the other half was added 20 minutes after the end of stage II. The latex was then cooled and filtered through a medium mesh filter. The latex exhibited the following properties: percent solids: 49.91%; pH: 6; $T_g$: 13.9° C.; MFT: <0° C.; and percent coagulum: 0.82%.

EXAMPLES 5 AND 6

Example 4 was repeated in examples 5 and 6 with the exception that the latex was prepared using the following amounts of material in each of these examples:

|  | Example 5 | Example 6 |
|---|---|---|
| Initiator Solution |  |  |
| DI water | 40.0 grams | 40.0 grams |
| Ammonium persulfate | 1.6 grams | 1.6 grams |
| Kettle Charge: |  |  |
| DI Water | 104.0 grams | 104.0 grams |
| Rhodapex CO-436 ™ | 3.0 grams | 2.0 grams |
| Pre-seeding |  |  |
| Vinyl acetate | 21.0 grams | 21.0 grams |
| Butyl acrylate | 9.0 grams | 9.0 grams |
| Pre-emulsion for Stage I |  |  |
| DI water | 104.0 grams | 104.0 grams |
| Rhodapex CO-436 ™ | 5.0 grams | 5.0 grams |
| Sodium carbonate | 0.4 grams | 0.4 grams |
| Vinyl acetate | 147.0 grams | 147.0 grams |
| Butyl acrylate | 63.0 grams | 63.0 grams |
| Acrylic acid | — | 1.5 grams |
| Pre-emulsion for Stage II |  |  |
| DI water | 40.0 grams | 40.0 grams |
| Rhodapex CO-436 ™ | 7.0 grams | 10.0 grams |
| Sodium carbonate | 0.6 grams | 0.6 grams |
| Butyl acrylate | — | 45.0 grams |
| Methyl methacrylate | 60.0 grams | — |
| CAM | 30.3 grams | 45.0 grams |
| Chaser solutions |  |  |
| DI water/t-butyl hydroperoxide* | 5.0 grams/0.45 grams | 5.0 grams/0.45 grams |
| DI water/sodium formaldehyde sulfoxylate | 5.0 grams/0.3 grams | 5.0 grams/0.3 grams |

*t-butyl hydroperoxide is supplied as a 70% solution in water

The latex obtained in example 5 exhibited the following properties: percent solids: 49.7% and $T_g$: 16.5° C. while the latex described in example 6 exhibited the following properties: percent solids: 50.58%; pH: 6; $T_g$: 5.9° C.; MFT: <0° C.; and percent coagulum: 0.33%.

EXAMPLE 7

Example 7 illustrates the preparation of a latex with a stage I to stage II weight ratio of 70/30. Example 4 was repeated with the exception that the latex was prepared using the following amounts of materials:

|  | Example 7 |
| --- | --- |
| Initiator Solution |  |
| DI water | 40.0 grams |
| Ammonium persulfate | 2.0 grams |
| Kettle charge |  |
| DI water | 100.0 grams |
| Rhodapex CO-436 ™ | 3.0 grams |
| Pre-seeding |  |
| Vinyl acetate | 21.0 grams |
| Butyl acrylate | 9.0 grams |
| Pre-emulsion for stage I |  |
| DI water | 100.0 grams |
| Rhodapex CO-436 ™ | 5.0 grams |
| Sodium carbonate | 0.4 grams |
| Vinyl acetate | 126.0 grams |
| Butyl acrylate | 54.0 grams |
| Acrylic acid | — |
| Pre-emulsion for Stage II |  |
| DI water | 60.0 grams |
| Rhodapex CO-436 ™ | 7.0 grams |
| Sodium carbonate | 0.6 grams |
| Butyl acrylate | 43.2 grams |
| Methyl methacrylate | 41.4 grams |
| Methacrylic acid | 0.9 grams |
| CAM II (Acrylated castor oil - Chemical registry no. 283149-92-8) | 4.5 grams |
| Chaser solutions |  |
| DI water/t-butyl hydroperoxide* | 5.0 grams/0.45 grams |
| DI water/sodium formaldehyde sulfoxylate | 5.0 grams/0.3 grams |

*t-butyl hydroperoxide is supplied as a 70% solution in water

In this example, the stage I pre-emulsion was added over 2.25 hours and 20.0 mL of the initiator solution was added over 2.75 hours. The stage II pre-emulsion was added over 1.5 hours and the remaining 12.0 mL of the initiator solution was added over 1.75 hours. This procedure afforded a latex with 48.9% solids, $T_g$ of 18.6° C. and MFT of 5° C.

EXAMPLE 8

Example 8 illustrates the preparation of a latex with a stage I to stage II weight ratio of 85/15. Example 4 was essentially repeated in example 8 with the exception that the following amounts of materials were used:

|  | Example 8 |
| --- | --- |
| Initiator Solution |  |
| DI water | 40.0 grams |
| Ammonium persulfate | 2.0 grams |
| Kettle charge |  |
| DI water | 100.0 grams |
| Rhodapex CO-436 ™ | 3.0 grams |

|  | Example 8 |
| --- | --- |
| Pre-seeding |  |
| Vinyl acetate | 21.0 grams |
| Butyl acrylate | 9.0 grams |
| Pre-emulsion for stage I |  |
| DI water | 100.0 grams |
| Rhodapex CO-436 ™ | 6.0 grams |
| Sodium carbonate | 0.5 grams |
| Vinyl acetate | 157.5 grams |
| Butyl acrylate | 67.5 grams |
| Acrylic acid | — |
| Pre-emulsion for Stage II |  |
| DI water | 60.0 grams |
| Rhodapex CO-436 ™ | 6.0 grams |
| Sodium carbonate | 0.5 grams |
| Butyl acrylate | 21.6 grams |
| Methyl methacrylate | 20.7 grams |
| Methacrylic acid | 0.45 grams |
| CAM II | 2.25 grams |
| Chaser solutions |  |
| DI water/t-butyl hydroperoxide* | 5.0 grams/0.45 grams |
| DI water/sodium formaldehyde sulfoxylate | 5.0 grams/0.3 grams |

*t-butyl hydroperoxide is supplied as a 70% solution in water

Stage I pre-emulsion was added to the reaction kettle over 2.6 hours and 26.0 mL of the initiator solution was added over 3.2 hours. The pre-emulsion for stage II was fed into the reaction kettle over 1.5 hours and the remaining 6.0 mL of the initiator solution was fed over 1.75 hours. This procedure afforded a latex with 48.8% solids, $T_g$ of 19.3° C., and MFT of 4.6° C.

EXAMPLE 9

Example 9 illustrates the preparation of a latex with a stage I to stage II weight ratio of 90/10. Example 4 was substantially repeated in example 9 with the exception that the latex was prepared at 65° C. using a redox initiator system and the following amounts of materials:

|  | Example 9 |
| --- | --- |
| Initiator Solution: |  |
| Oxidizing components: |  |
| DI water | 30.0 grams |
| Ammonium persulfate | 0.57 grams |
| t-butyl hydroperoxide* | 1.02 grams |
| Reducing components: |  |
| DI water | 30.0 grams |
| Sodium metabisulfite | 1.12 grams |
| Kettle charge: |  |
| DI water | 90.0 grams |
| Rhodapex CO-436 ™ | 3.0 grams |
| Iron(II) sulfate heptahydrate | 0.004 grams |
| Pre-emulsion for stage I |  |
| DI water | 130 grams |
| Rhodapex CO-436 ™ | 6.0 grams |
| Sodium carbonate | 0.5 grams |
| Vinyl acetate | 175.5 grams |
| Butyl acrylate | 94.5 grams |
| Pre-emulsion for Stage II |  |
| DI water | 30.0 grams |

-continued

|  | Example 9 |
| --- | --- |
| Rhodapex CO-436 ™ | 6.0 grams |
| Sodium carbonate | 0.5 grams |
| Butyl acrylate | 12.0 grams |
| Methyl methacrylate | 15.0 grams |
| CAM II-3.1 (Acrylated castor oil) | 3.0 grams |

*t-butyl hydroperoxide is supplied as a 70% solution in water

Pre-seeding was achieved by adding 45.0 grams of the stage I pre-emulsion and 6.0 mL each of the oxidizing and reducing components of the initiator system to the reaction kettle at 65° C. This was allowed to react for 20 minutes. The remaining stage I pre-emulsion was then fed into the reactor over a period of 2 hours along with 16.0 mL each of the oxidizing and reducing components of the initiator system which were concurrently fed into the reaction flask over 3 hours. After the initiator feed was complete, the stage II pre-emulsion was introduced over 0.75 hours and the remaining initiator solutions were co-fed into the reactor over 1.5 hours. The reaction was allowed to post react for 1 hour and then cooled and filtered. This procedure yielded a latex with 49.2% solids, particle size of 147 nm and $T_g$ of 5.0° C.

EXAMPLE 10

Example 10 illustrates the preparation of a latex with a stage I to stage II weight ratio of 95/5. Example 4 was essentially repeated with the exceptions that the latex was prepared at 65° C. using a redox initiator system and the following amounts of materials:

|  | Example 10 |
| --- | --- |
| Initiator Solution: | |
| Oxidizing components: | |
| DI water | 20.0 grams |
| Ammonium persulfate | 0.348 grams |
| t-butyl hydroperoxide* | 0.69 grams |
| Reducing components: | |
| DI water | 20.0 grams |
| Sodium formaldehyde sulfoxylate | 0.6 grams |
| Kettle Charge: | |
| DI water | 90.54 grams |
| Rhodapex CO-436 ™ | 0.75 grams |
| Igepal CO-887 ™ | 1.87 grams |
| Pre-emulsion for stage I | |
| DI water | 140.83 grams |
| Rhodapex CO-436 ™ | 2.63 grams |
| Igepal CO-887 ™ | 6.55 grams |
| Ammonium bicarbonate | 0.5 grams |
| Vinyl acetate | 206.4 grams |
| 2-ethylhexyl acrylate | 79.8 grams |
| Acrylic acid | 0.3 grams |
| Pre-emulsion for Stage II | |
| DI water | 30.0 grams |
| Rhodapex CO-436 ™ | 2.08 grams |
| Ammonium bicarbonate | 0.5 grams |
| Methyl methacrylate | 3.0 grams |
| CAM II-3.1 | 12.0 grams |

*t-butyl hydroperoxide is supplied as a 70% solution in water

Pre-seeding was achieved by adding 45.75 grams of the stage I pre-emulsion and 4.0 mL each of the oxidizing and reducing components of the initiator system to the reaction kettle at 65° C. This was allowed to react for 20 minutes. The remaining stage I pre-emulsion was then fed into the reactor over a period of 3 hours along with 10.0 mL each of the oxidizing and reducing components of the initiator system which were concurrently fed into the reaction flask over 4 hours. After the initiator feed was complete, the stage II pre-emulsion was introduced over 0.5 hours and the remaining initiator solutions (6.0 mL each of the oxidizing and reducing solutions) were co-fed into the reactor for 1 hour. The latex was cooled to room temperature and filtered through a medium mesh filter immediately after the initiator co-feed for stage II was complete. This procedure afforded a latex with 49.7% solids, particle size of 150 nm, MFT of 2.5° C. and $T_g$ of 13.4° C.

EXAMPLE 11

Example 11 illustrates the preparation of a latex with a stage I to stage II ratio of 98/2. Example 4 was essentially repeated with the exceptions that the latex was prepared at 65° C. using a redox initiator system and the following amounts of materials:

|  | Example 11 |
| --- | --- |
| Initiator Solution: | |
| Oxidizing components: | |
| DI water | 20.0 grams |
| Ammonium persulfate | 0.348 grams |
| t-butyl hydroperoxide* | 0.69 grams |
| Reducing components: | |
| DI water | 20.0 grams |
| Sodium formaldehyde sulfoxylate | 0.6 grams |
| Kettle Charge: | |
| DI water | 90.0 grams |
| Rhodapex CO-436 ™ | 1.96 grams |
| Igepal CO-887 ™ | 1.84 grams |
| Pre-emulsion for Stage I | |
| DI water | 140.00 grams |
| Rhodapex CO-436 ™ | 0.98 grams |
| Igepal CO-887 ™ | 5.48 grams |
| Ammonium bicarbonate | 0.50 grams |
| Vinyl acetate | 211.68 grams |
| 2-ethylhexyl acrylate | 81.73 grams |
| Acrylic acid | 0.30 grams |
| Pre-emulsion for Stage II | |
| DI water | 30.0 grams |
| Rhodapex CO-436 ™ | 0.78 grams |
| Igepal CO-887 ™ | 1.95 grams |
| Ammonium bicarbonate | 0.5 grams |
| CAM II-3.1 | 6.0 grams |

*t-butyl hydroperoxide is supplied as a 70% solution in water

Pre-seeding was achieved by adding 45.0 grams of the stage I pre-emulsion and 4.0 mL each of the oxidizing and reducing components of the initiator system to the reaction kettle at 65° C. This was allowed to react for 20 minutes. The remaining stage I pre-emulsion was then fed into the reactor over a period of 2 hours along with 12.0 mL each of the oxidizing and reducing components of the initiator system which were concurrently fed into the reaction flask over 3 hours. After the initiator feed was complete, the stage II pre-emulsion was introduced over 0.75 hours and the remaining initiator solutions were co-fed into the reactor over 1 hour. The latex was cooled to room temperature and filtered through a medium mesh filter immediately after the initiator co-feed for stage II was complete. This procedure yielded a latex with 49.6% solids, particle size of 212 nm and $T_g$ of 9.6° C.

EXAMPLE 12

Example 12 illustrates the preparation of a latex with a stage one to stage two ratio (w/w) of 95/5. Example 1 was essentially repeated with the exceptions that the latex was prepared at 65° C. using a redox initiator system and the following amounts of materials:

| | |
|---|---|
| Initiator Solution: | |
| Oxidizing components: | |
| DI water | 20.0 grams |
| Ammonium persulfate | 0.348 grams |
| t-butyl hydroperoxide* | 0.69 grams |
| Reducing components: | |
| DI water | 20.0 grams |
| Sodium formaldehyde sulfoxylate | 0.60 grams |
| Kettle charge: | |
| DI water | 90.54 grams |
| Rhodapex CO-436 | 0.75 grams |
| Igepal CO-887 | 1.87 grams |
| Pre-emulsion for stage I | |
| DI water | 140.83 grams |
| Rhodapex CO-436 | 2.63 grams |
| Igepal CO-887 | 6.55 grams |
| Ammonium bicarbonate | 0.50 grams |
| Vinyl acetate | 206.40 grams |
| 2-ethylhexyl acrylate | 79.80 grams |
| Acrylic acid | 0.30 grams |
| Pre-emulsion for Stage II | |
| DI water | 30.0 grams |
| Rhodapex CO-436 | 2.08 grams |
| Ammonium bicarbonate | 0.5 grams |
| Methyl methacrylate | 3.0 grams |
| CAM XV (Diacrylate of soybean oil trimethylolpropane monoglyceride) | 12.0 grams |

*t-butyl hydroperoxide is supplied as a 70% solution in water

Pre-seeding was achieved by adding 45.76 grams of the stage I pre-emulsion and 4.0 mL each of the oxidizing and reducing components of the initiator system to the reaction kettle at 65° C and reacting for 20 minutes. The remaining stage I pre-emulsion was then fed into the reactor over a period of 3.0 hours along with 10.0 mL each of the oxidizing and reducing components of the initiator system which were concurrently fed into the reaction flask over 4.0 hours. After the initiator feed was complete, the stage II pre-emulsion was introduced over 30 minutes and the remaining initiator solutions were co-fed into the reactor over 1.0 hour. The latex was allowed to cool to room temperature and filtered through a medium mesh filter immediately after the initiator co-feed for stage II was complete. This procedure afforded a latex with 49.2% solids, a particle size of 151 nm, a MFT of 1.0° C. and a $T_g$ of 10.5° C.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof. Accordingly, the scope of the invention is to be determined by following claims rather than the foregoing description.

What is claimed is:

1. A process for forming a latex polymer comprising:
   polymerizing an ethylenically unsaturated monomer suitable for forming a latex polymer in a first stage of an emulsion polymerization in the presence of a hybrid surfactant;
   adding an acrylated fatty acid or oil; and
   polymerizing said fatty acid or oil derivative in a second stage of said emulsion polymerization.

2. A process as defined in claim 1 wherein said ethylenically unsaturated monomer is selected from the group consisting of vinyl acetate, vinyl chloride, vinyl ester of a saturated tertiary branched carboxylic acid, acrylonitrile, acrylamide, 2-ethylhexyl acrylate, 2-ethylhexyl methacrylate, 2-hydroxyethyl acrylate, 2-hydroxyethyl methacrylate, glycidyl acrylate, glycidyl methacrylate, acrylic acid, methacrylic acid, butyl acrylate, butyl methacrylate, methyl methacrylate, methyl acrylate, para-acetoxystyrene, and styrene.

3. The process of claim 1 further comprising adding a second surfactant to said first stage of said emulsion polymerization.

4. The process of claim 1 wherein the acrylated fatty acid comprises acrylated castor oil.

5. The process of claim 1 wherein additional ethylenically unsaturated monomer is polymerized in the second stage.

6. The process of claim 1 wherein the ethylenically unsaturated monomer comprises vinyl acetate.

7. The process of claim 1 further comprising polymerizing a second ethylenically unsaturated monomer in said first polymerization step.

\* \* \* \* \*